(12) United States Patent
Richardson (10) Patent No.: US 9,086,394 B2
(45) Date of Patent: Jul. 21, 2015

(54) MULTI-FUNCTION DISPENSE HEAD

(71) Applicant: Accel Biotech, Inc., Los Gatos, CA (US)

(72) Inventor: Bruce Richardson, Los Gatos, CA (US)

(73) Assignee: Accel Biotech, Inc., Las Gatos, CA (US)

( * ) Notice: Subject to any disclaimer, the term of this patent is extended or adjusted under 35 U.S.C. 154(b) by 74 days.

(21) Appl. No.: 14/062,567

(22) Filed: Oct. 24, 2013

(65) Prior Publication Data

US 2014/0112839 A1    Apr. 24, 2014

Related U.S. Application Data (60) Provisional application No. 61/718,112, filed on Oct. 24, 2012.

(51) Int. Cl.
| | | |
|---|---|---|
| *B01L 3/02* | (2006.01) | |
| *G01N 35/00* | (2006.01) | |
| *G01N 35/10* | (2006.01) | |

(52) U.S. Cl.
CPC ........ *G01N 35/0099* (2013.01); *G01N 35/1065* (2013.01); *G01N 2035/103* (2013.01)

(58) Field of Classification Search
CPC ....... B01L 3/02; B01L 3/0275; B01L 3/0227; B01L 3/0279; G01N 35/10; G01N 35/1002; G01N 2035/103; G01N 35/1065; G01N 35/0099
USPC ................. 422/511, 524–525, 509, 521, 501; 73/863.32, 864, 864.01, 864.11, 73/864.13, 864.14, 864.16, 864.17
See application file for complete search history.

(56) References Cited

U.S. PATENT DOCUMENTS

| | | | |
|---|---|---|---|
| 4,824,642 A * | 4/1989 | Lyman et al. ................. | 422/516 |
| 4,830,832 A | 5/1989 | Arpagaus et al. | |
| 5,827,745 A * | 10/1998 | Astle .............................. | 436/54 |
| 6,182,719 B1 * | 2/2001 | Yahiro ........................ | 141/130 |
| 6,374,683 B1 | 4/2002 | Hunicke-Smith et al. | |
| 6,415,669 B1 * | 7/2002 | Carl ........................... | 73/864.14 |
| 6,734,683 B2 | 5/2004 | Hash | |
| 6,793,891 B2 | 9/2004 | Yiu | |
| 6,982,063 B2 * | 1/2006 | Hamel et al. .................. | 422/511 |
| 7,189,369 B2 * | 3/2007 | Higuchi ....................... | 422/511 |
| 7,220,384 B2 | 5/2007 | Muller | |
| 8,697,012 B2 * | 4/2014 | Ikushima .................... | 422/511 |
| 2001/0039843 A1 | 11/2001 | Schoeppe | |
| 2006/0144169 A1 * | 7/2006 | Porat et al. ................ | 73/864.14 |

\* cited by examiner

*Primary Examiner* — Brian R Gordon
(74) *Attorney, Agent, or Firm* — Thomas Schneck (57) ABSTRACT

A multi-function dispense head operable by a single motor. The dispense head includes a pipette housing having carriage driven pipette rods and carriage driven pistons and a wash/ejector head movable by the pistons. The carriage is attached to the pipette rods and vertically moves the rods through the pipette housing as needed for various pipette functions. The pistons are pushed into movement by the carriage and, in a lower position, into contact with a lower ledge along a bottom portion of the movable head forcing the lower ledge downwardly to eject pipette tips. The pistons also move the wash/ejector head when the movable head performs a wash function.

20 Claims, 7 Drawing Sheets

MULTI-FUNCTION DISPENSE HEAD

CROSS-REFERENCE TO RELATED APPLICATIONS

This application claims the benefit of priority from U.S. provisional application No. 61/718,112, filed on Oct. 24, 2012, which is hereby incorporated by reference.

TECHNICAL FIELD

The technical field relates to analytical chemistry processing and clinical and research laboratory workstations capable of performing multiple functions and, more particularly, to mechanisms for pipetting, pipette tip ejection and washing.

BACKGROUND ART

Many types of automated pipetting systems used for the aspiration and dispensing of relatively small quantities of liquids into the wells of plates such as microplates and apparatuses for cleaning wells are known in the art. Examples of liquids being dispensed include biological samples, solvents and reagents. Some or all of the liquid is normally drawn by suction through disposable pipette tips from one set of plates or a reservoir of sample and is released through the pipette tips into the wells of other plates. After use, the pipette tips are ejected and replaced with new ones and the sample containing wells are washed.

For example, U.S. Patent Application No. 2001/0039843 to Schoeppe discloses an automatic pipettor with a single row, multi-channel pipetting head and pipette tip ejector mechanism. The tip ejector mechanism includes a shaft oriented in the direction of a row of pipettes and push-off units fastened to the shaft in offset positions, each of which successively comes into contact with a strip-off unit guided in the direction of the pipettes during shaft rotation to strip tips.

U.S. Pat. No. 6,793,891 to Yiu discloses an automated pipetting and tip engagement and disengagement mechanism including a pipette block that engages pipettes and a locking plate system that engages pipette tips. The pipette block moves vertically with respect to the locking plate system to apply or decrease pressure within the pipette tip causing the pipette tip to dispense or aspirate fluid. When disengaging the pipette tips, the locking plate assembly holds the tips in place as the pipette block is lifted so that it travels sufficiently high to disengage the tips.

U.S. Pat. No. 6,734,683 to Hunicke-Smith et al. and U.S. Pat. No. 4,830,832 to Arpagus et al. also disclose automated pipetting apparatuses.

U.S. Pat. No. 7,220,384 to Muller discloses a washing and extracting head for an apparatus designed to wash microplates. The head is movable above the microplates and includes dispensing and suction tubes associated in pairs, the number of pairs being equal to the number of wells per row.

It is desirable to perform pipetting, tip ejection and washing operations rapidly and efficiently in a pipetting system.

An object of the present invention is to provide a new and improved apparatus or system for performing pipetting, pipette tip ejection and/or washing of sample wells.

SUMMARY

A multi-function dispense head operable by a single motor comprises a pipette housing having carriage driven pipette rods and carriage driven pistons disposed in and extending from the housing and a movable wash/ejector head adjacent to the housing and movable by the pistons. The carriage is attached to the pipette rods which extend through the pipette housing and moves the pipette rods linearly through the pipette openings in the pipette housing when pipettes are used for aspiration and dispensation of fluid. The carriage pushes the pistons into movement through a pair of piston rod openings in the pipette housing by the carriage. The movable head has a lower ledge along a bottom portion which is disposed beneath the lower surface of the pipette housing. The pistons make contact with the lower ledge when the carriage moves to a lower position. The piston contact and downward force cause the movable head to move downwardly.

In the lower position, the lower ledge makes contact with pipette tips connected to the pipette rods and urges the pipette tips off the pipette rods. Each ledge opening has a diameter slightly smaller than a diameter of an upper portion of a pipette tip so that the ledge is able to push down upon the tips when moving. In the lowered position the movable head is capable of providing a wash function with dispensation and aspiration systems.

DETAILED DESCRIPTION

Figure 1:
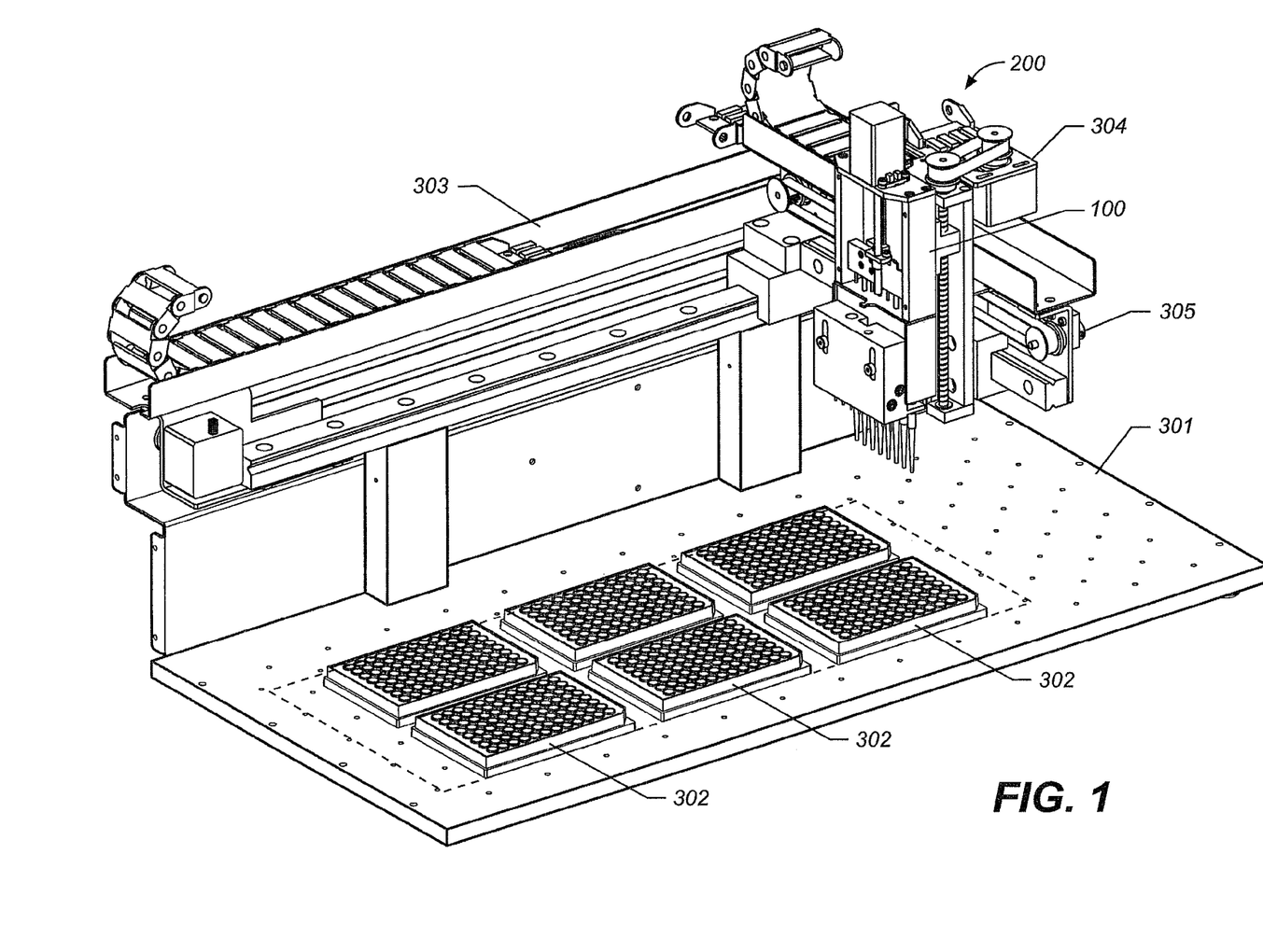
FIG. 1 is a perspective view of a multi-function dispense head of a fluid handling system.
Figure 3:
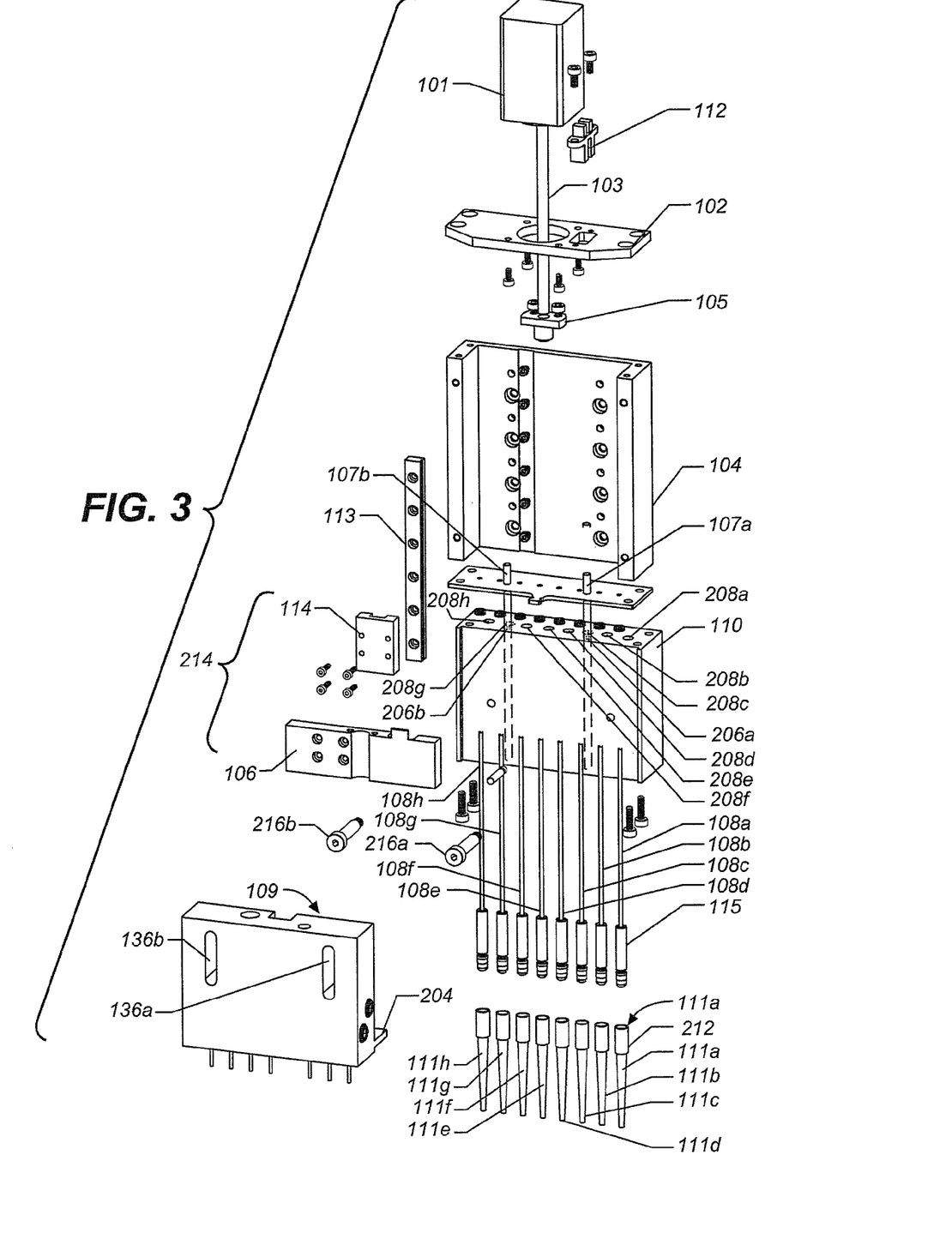
FIG. 3 is an exploded view of the multi-function dispense head of FIG. 2.

With reference to FIG. 1, there is seen a multi-axis robotic system 200 featuring an automated multi-function processing head 100. The multi-function dispense head 100 performs multiple functions which may all be actuated with one motor and drive system. The multi-function dispense head 100 could be mounted to many types of special drive systems including an x, y, z, robot, an r theta system, and/or any other motion system. The motor coupled to an actuator is used to control the multiple functions including fluid aspiration, fluid dispensation, tip ejection, wash head distension, and wash head retraction. Referring to FIG. 3, the function of coupling disposable pipette tips 111 to pipette couplings 115 of pipette rods 108 is performed using an external robotic system.

Referring back to FIG. 1, the system also includes a laboratory work station having a table 301 for supporting microtiter plates 302 and other fluid receptacles, a movable arm 303, a z axis drive mechanism 304, a Y axis drive mechanism 305, the multi-function head 100 affixed for reciprocal movement along the arm. The workstation combines into a single programmable system the capabilities for automation of a wide range of bio analytical procedures including sample pipetting, serial dilution, reagent additions, mixing, reaction timing and washing of reaction vessels. The multi-function dispense head 100 is adapted to transfer liquid from one location to another automatically in accordance with user programmed instructions. The work station is designed for interactive connection with a remote computer.

Figure 2:
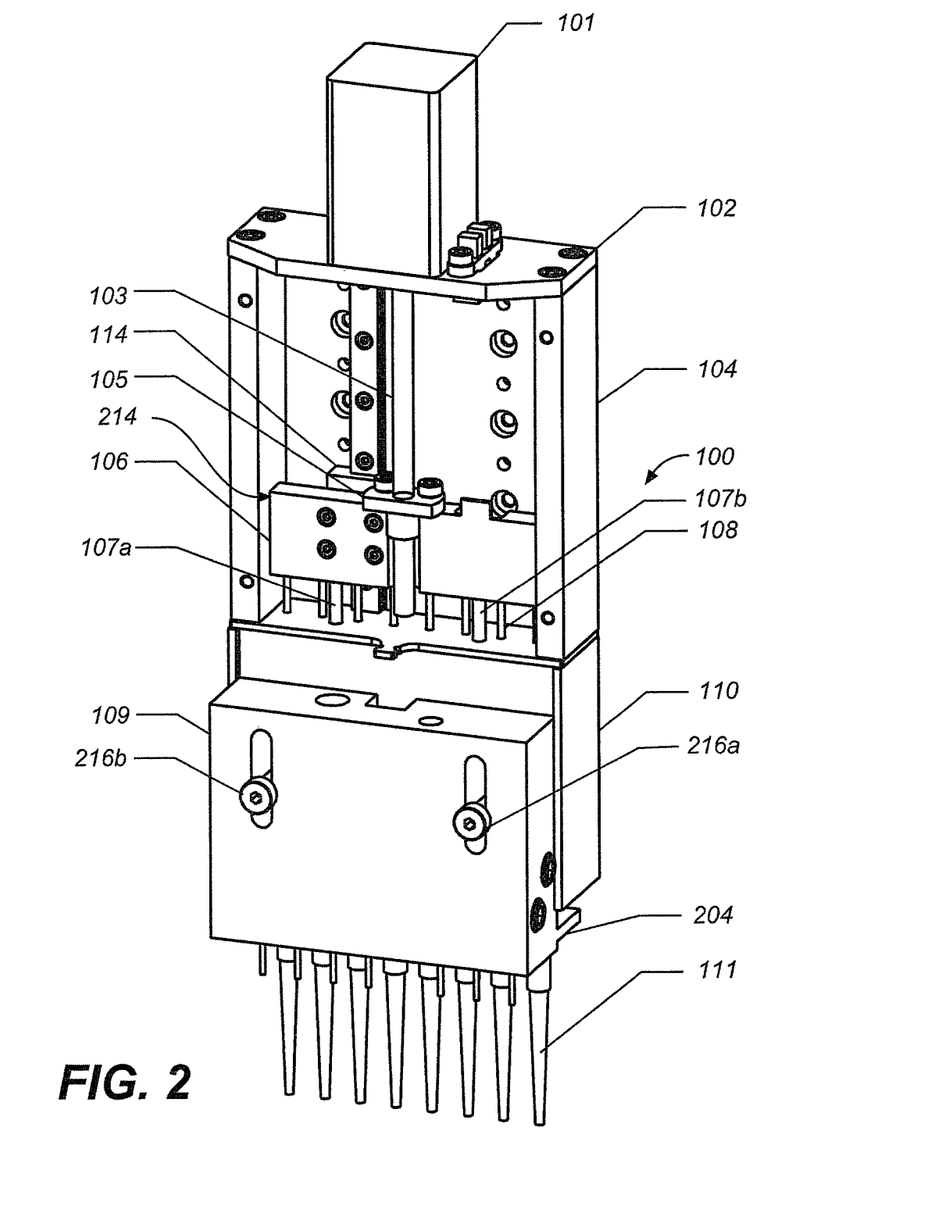
FIG. 2 is a perspective view of the multi-function dispense head of FIG. 1.
Figure 4A:
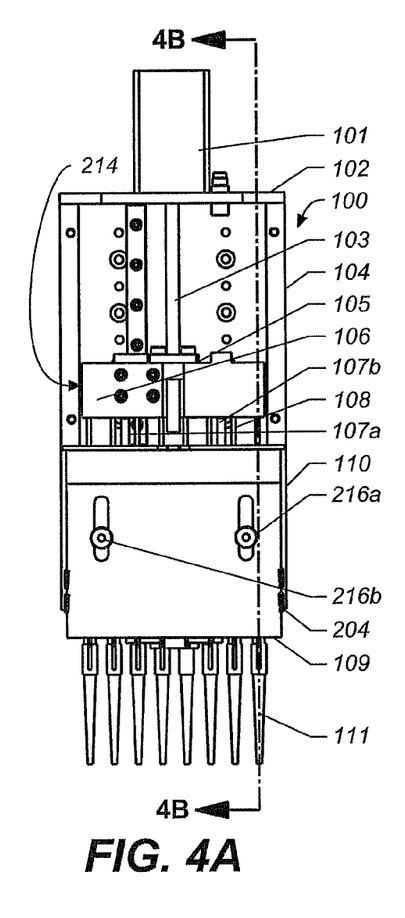
FIG. 4A is a front view of the multi-function head of FIG. 2.
Figure 4B:
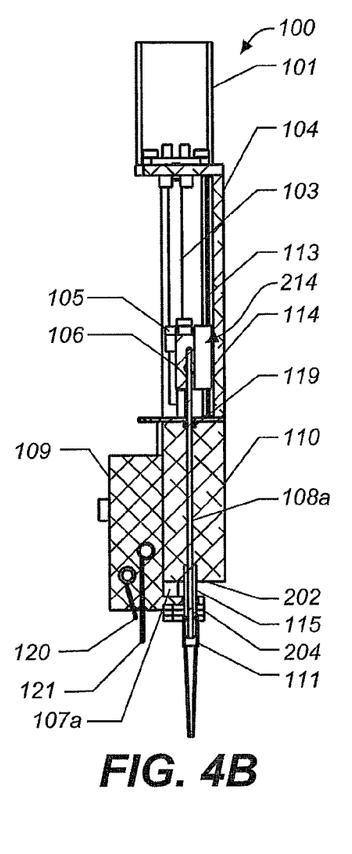
FIG. 4B is a cross sectional view of FIG. 4A taken along the line 4B-4B.

With reference to FIGS. 2-4, multi-function dispense head 100 has a pipette tip ejection mechanism featuring a carriage driven wash/ejector movable head 109 with a lower ledge 204 along a bottom portion of the ejector head used to urge or push disposable tips 111 off carriage driven pipette rods 108 of a pipette housing 110. Pipette housing 110 has a pair of ledge contactable rods/pistons 107a, 107b disposed within a pair of piston openings 206a, 206b, respectively, that are pushed into contact with the lower ledge 204 by a motor driven carriage 214. The pipette housing 110 also has a plurality of vertically pipette passages 208a-h extending through the housing and pipette rods 108a-h, each pipette rod disposed in one vertically extending passage and extending past a lower surface 202 of the housing. The pipette tips 111a-h are removably connected to pipette rods 108a-h at pipette tip couplings 115 (FIG. 3). The lower ledge 204 is disposed beneath lower surface 202 of the pipette housing 110 and has openings 210a-h in vertical alignment with the pipette housing passages 208a-h. The pipette rods 108a-h pass through the housing passages 208a-h and openings 210a-h of the wash head. Each opening 210 has a diameter slightly smaller than a diameter of an upper portion 212 of a pipette tip 111.

Figure 8A:
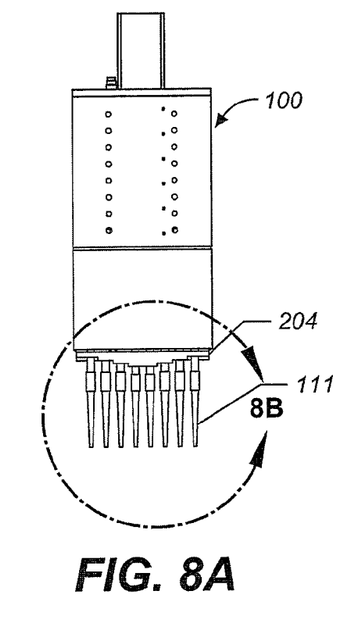
FIG. 8A is a front plan view of the multi-function dispense head of FIG. 2.
Figure 8B:
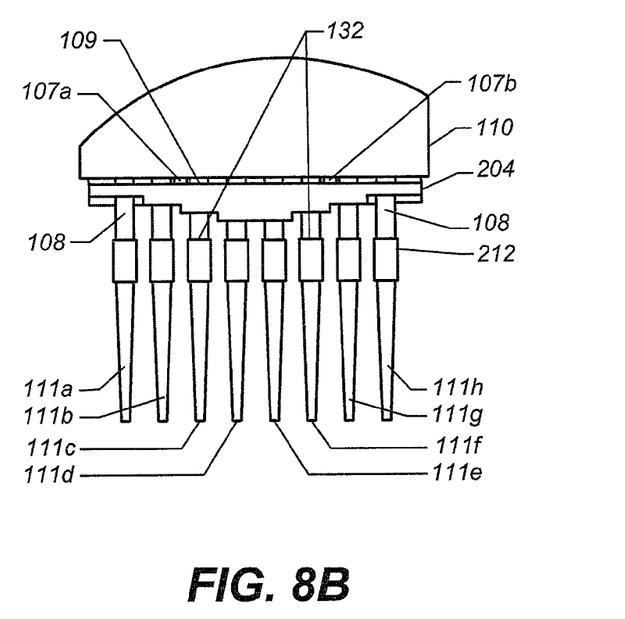
FIG. 8B is a magnified view of section 8B of FIG. 8A.
Figure 8C:
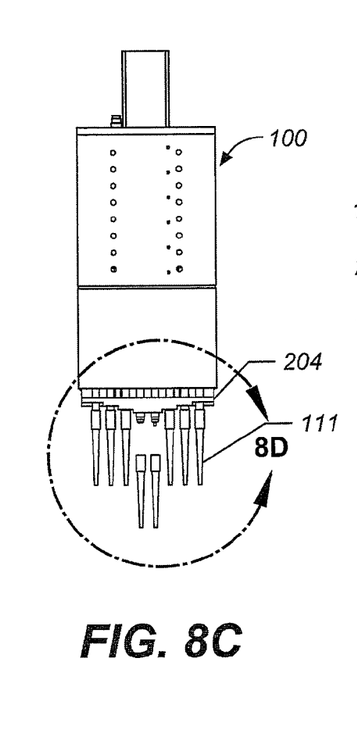
FIG. 8C is another front plan view of the multi-function dispense head of FIG. 2.
Figure 8D:
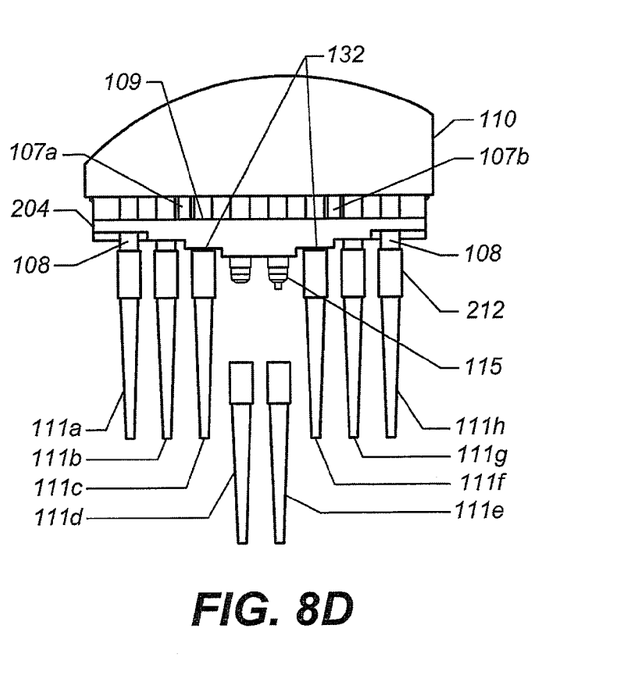
FIG. 8D is a magnified view of section 8D of FIG. 8C.

Pistons 107a, 107b are urged downwardly from a first position seen in FIGS. 8a and 8b, to a lower position seen in FIGS. 8c and 8d. The pistons 107a, 107b push the lower ledge 204 downwardly and into contact with a top 132 of the disposable tips 111 thereby urging the pipette tips 111 in the vertical direction of the moving pistons and ejecting pipette tips 111 from the pipettes 108. Wash head 109 moves downwardly relative to the pipette housing 110 as the pistons 107 push down against the ledge 204.

Figure 5:
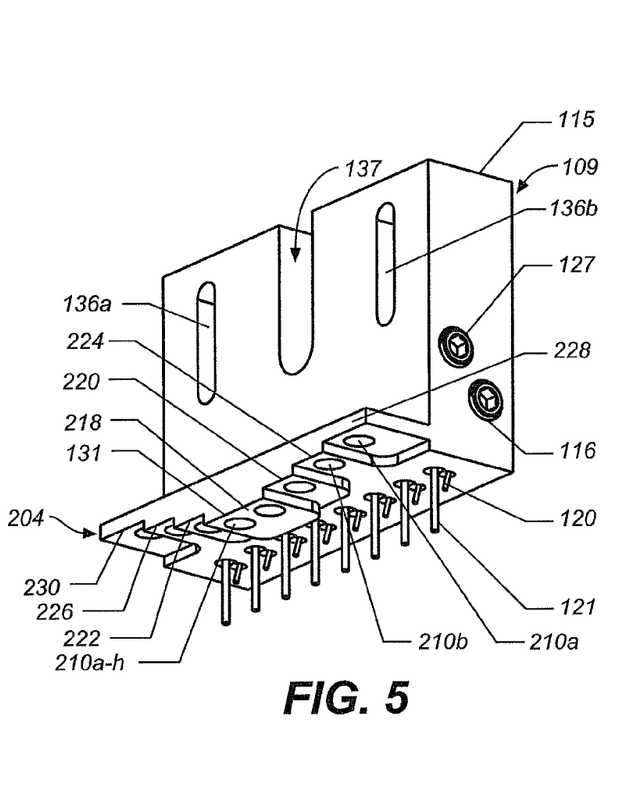
FIG. 5 is a perspective view of the movable head of FIG. 2.
Figure 6A:
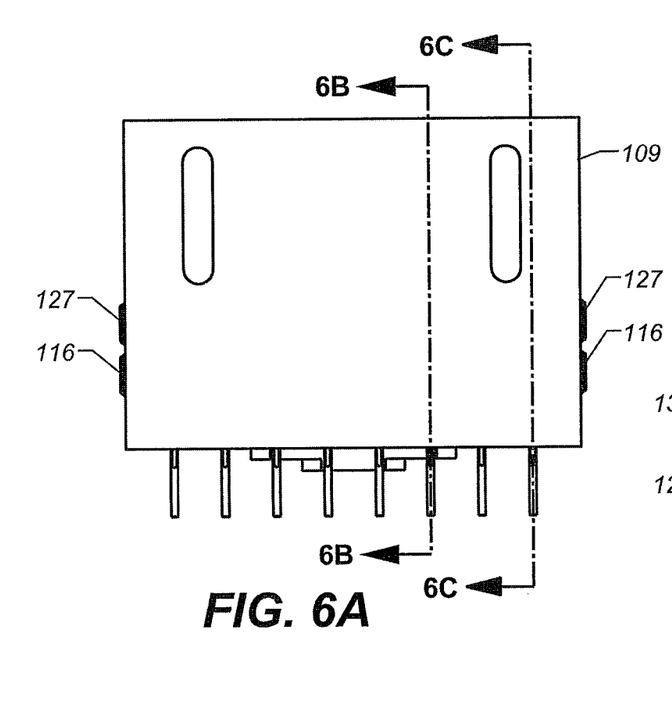
FIG. 6A is a front plan view of the movable head of FIG. 2.
Figure 6B:
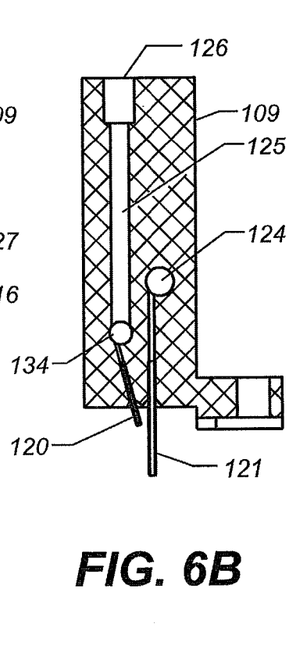
FIG. 6B is a cross-sectional view of the movable head of FIG. 6A taken along the line 6B-6B.
Figure 6C:
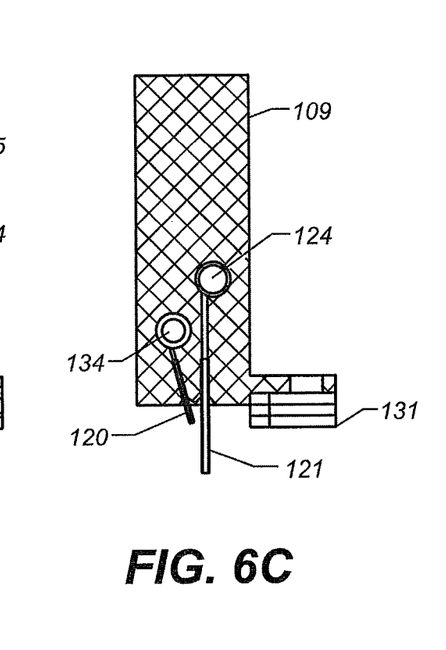
FIG. 6c is a cross-sectional view of the movable head of FIG. 6A taken along the line 6C-6C.
Figure 7A:
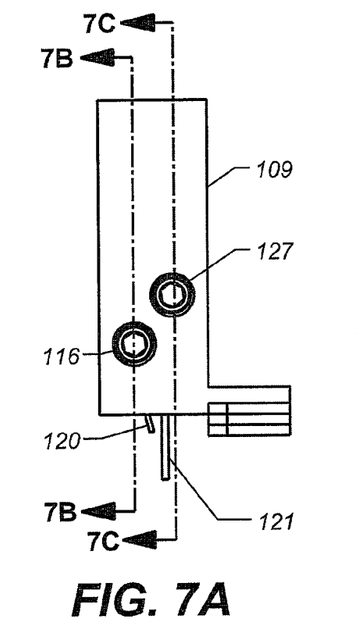
FIG. 7A is a side plan view of the wash head of FIG. 5.
Figure 7B:
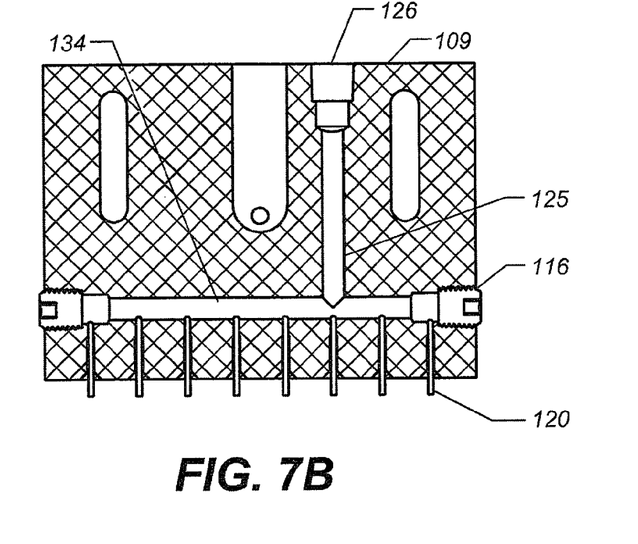
FIG. 7B is a sectional view of the wash head of FIG. 2 taken along the line 7B-7B.
Figure 7C:
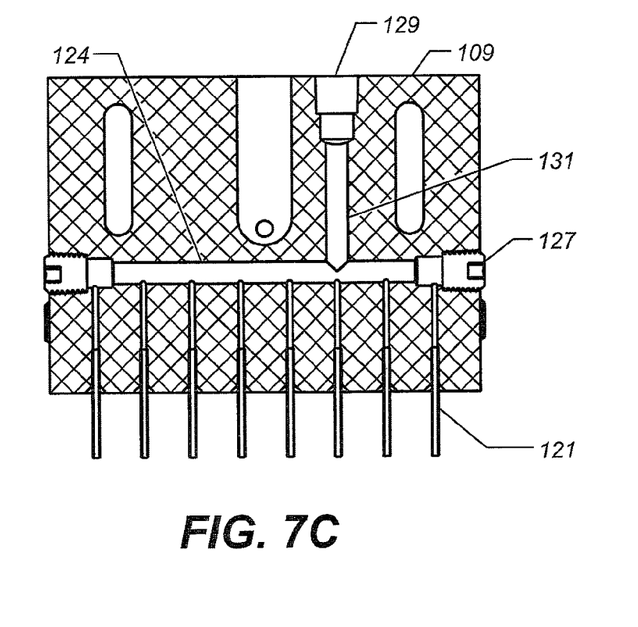
FIG. 7C is a sectional view of the wash head of FIG. 2 taken along the line 7C-7C.

With reference to FIGS. 3 and 5, wash head 109 includes slots 136a and 136b which receive screws 216a and 216b connected to pipette housing 210. The wash head is movable relative to the pipette housing a distance defined by the slots 136.

With reference to FIGS. 2-4, a vertically movable motor driven carriage 214 drives the pistons 107a, 107b through the piston openings 206a, 206b from an upper position (FIGS. 8A-8B) to a lower position (FIGS. 8C-D). The carriage 214 pushes the pipette rods 107a, 107b to the lower position and downwardly against the ledge 204 at a location adjacent the ledge openings 210a-h, thereby urging the ledge of wash head 109 against the pipette tips 111 and causing ejection of the pipette tips as the lower ledge makes contact with and is urged downwardly on the disposable tips 111.

The carriage 214 is moved by motor 101 to push rods 107a, 107b into contact with the lower ledge 204 of the wash plate. The carriage 214 includes carriage bar 106 and carriage plate 114. Carriage bar 106 is connected to a linear bearing 113 via carriage plate 114 which is driven by a lead screw 103 via rotation provided by the motor 101. The lead screw is connected to nut 105. The motor 101 moves carriage bar 106 via the rotation of the motor 101 to a lower extent of the motion. The carriage bar 106 pushes on rods 107 that push on the wash head 109 at the lower ledge that ejects the tips 111.

The motor 101 includes a home position sensor 112 for the drive mechanism, for example, the lead screw 103 and nut 105. The motor is mounted to a motor mount 102 which is connected to pipette actuator block 104. Lead screw 103 extends from motor 101 to the pipette head 110 in the pipette actuator block 104. Linear bearing 113 is mounted to the pipette actuator block 104 and linear carriage plate 114 is movable along linear bearing 113.

With reference to FIGS. 5 and 8A-D, the lower ledge 204 of the wash head 109 has a stepped profile or stepped cross section to reduce the force of ejection of tips 111a-h. The force required to eject the tips 111, typically eight tips at a time, can be excessive. To reduce the force, fewer than eight tips are ejected at one time. In one example, only two tips 111 are ejected at each successive position of the wash head 109. First step 218 of lower ledge 204 makes contact with two center pipette tips 111d, 111e to eject them. As the wash head 109 is first lowered, steps 220 and 222 make contact with pipette tips 111c, 111f, respectively, to eject them. The wash head is lowered further so that steps 224 and 226 make contact with pipette tips 111b, 111g, respectively, to eject them. The wash head is lowered again so that steps 228 and 230 make contact with pipette tips 111a, 111h, respectively, to eject them. Once the wash head 109 moves down successive positions all of the tips 111a-h are ejected by the steps of the lower ledge by force exerted on a flat of the head 132 (FIG. 8B) of the tips 111.

With reference to FIG. 5, a spring mechanism may be used to retract the wash head 109. The spring mechanism may be disposed in a spring holder 137 such as the one disposed in between slots 136 in FIG. 5. When the wash head is retracted upwardly with the spring, it pushes the rods 107a, 107b upwardly to a start position.

With reference to FIGS. 2-4, motor 101 is used to linearly move pipette rods 108a-h. Pipette rods 108a-h may be moved into a fluid source to create a vacuum or pressure that is used to aspirate fluid into the tips 111 and to a well to dispense fluids from the tips. When causing pipette rod/pipette movement the carriage 214 moves vertically along screw 103 in positions on the screw above positions from where it pushes pistons 107. Pipette rods 108a-h are driven by the carriage 214 and move upwardly and downwardly with the carriage through pipette head 110. Rods 108a-h attached to carriage bar 106 are sandwiched between carriage bar 106 and carriage plate 108. In one example, rods 108a-h may be epoxied or bonded onto the carriage and, in another example, are attached via e-rings to the carriage. Other attachment means, for example, a set screw, may be used. Rods 108 are sealed at the top of the piston by an o-ring seal 119.

Referring to FIGS. 6A-C and FIGS. 7A-C, the wash head 109 includes a separate set of wash tips 120 used to flush and wash reaction vessels and aspirate tips 121 to aspirate fluid at the control of the user. The wash head 101 includes a horizontal fluid distribution manifold 134 (FIG. 7B) having a plug 116, the manifold is able to deliver wash fluids to wells or vials 302 below. The wash fluid travels from a fluid source (not shown) to a fluid source connector 126 through the vertical vessel 125 and then through the horizontal distribution manifold 134 to the wash tips 120. To remove the wash or other fluids from the wells or vials 302 a second set of tips, aspirate tips 121, are used. Aspirate tips 121 are connected to a similar manifold system as the wash dispense tips 120. Aspirate tips 121 are connected to a horizontal vacuum manifold 124 having a plug 127. The vacuum manifold 124 is connected to a vacuum source (not shown) via vacuum source connector 129 and vertical vessel 131 to communicate with the vacuum source to remove fluid from the wells or vials 302.

When performing a wash function, the wash head 109 is lowered and retracted by the same linear drive system and motor 101 as in the tip ejection process. Carriage bar 106 pushes down on the rods 107 in the manner described with regard to ejecting pipette tips to lower the wash head 109 when washing is to occur.

What is claimed is:

1. A multi-function dispense head, comprising:
a pipette housing having a plurality of vertically extending pipette rod passages through the housing and pipette rods, each pipette rod disposed in one vertically extending passage and extending past a lower surface of the housing, the pipette rods removably connected to pipette tips, and a pair of ledge contactable pistons movably disposed within a pair of piston openings in the pipette housing;
a movable head having a lower ledge along a bottom portion of the movable head, the lower ledge disposed beneath the lower surface of the pipette housing and having openings through which pipette rods pass in vertical alignment with the pipette passages, each opening having a diameter slightly smaller than a diameter of an upper portion of a pipette tip, the movable head vertically movable relative to the pipette housing; and
a vertically movable motor driven carriage, the carriage operable to push the ledge contactable pistons through the piston openings from an upper position out of contact with the lower ledge to a lower position in contact with the lower ledge, thereby moving the movable head downwardly and urging the lower ledge against pipette tips to eject pipette tips.

2. The multi-function dispense head of claim 1 wherein the vertically movable motor driven carriage is attached to the pipette rods and is operable to linearly move the pipette rods upwardly and downwardly through the pipette head to different positions.

3. The multi-function dispense head of claim 1 further comprising a motor driving the carriage.

4. The multi-function dispense head of claim 1 wherein the lower ledge has a stepped cross-section.

5. The multi-function dispense head of claim 4 wherein the stepped cross-section decreases in height from the center to the edges such that contact of the lower ledge with the pipette tips is first made at the center of the lower ledge.

6. The multi-function dispense head claim 5 wherein there is a central step and three pairs of steps on each side of the center step, each pair of steps decreasing in height towards the edge.

7. The multi-function dispense head of claim 1 further comprising wash tips and aspirate tips extending from a lower surface of the movable head, the wash tips and aspirate tips movable in a vertical direction with the movable head when the motor driven carriage moves the movable head via the pistons.

8. The multi-function dispense head of claim 7 further comprising a fluid source connected to the wash tips and a vacuum supply connected to the aspirate tips.

9. The multi-function dispense head of claim 1 further comprising a spring return urging the movable head to the upper position from the lower position.

10. The multi-function dispense head of claim 1 wherein the movable head is movably connected to the pipette housing via a pair of slots on the movable head receiving a pair of screws connected to the pipette housing, the screws disposable in different positions in the slot as the moveable head moves wherein an extent of motion of the movable head relative to the pipette housing is defined by the distance within the pair of slots.

11. A multi-function dispense head, comprising:
a pipette housing having pipette rods extending from the pipette housing, pipette tips removably connectable to pipette rods, and ledge contactable pistons vertically movable within piston openings in the pipette housing;
a movable head having a lower ledge along a bottom portion of the movable head, the lower ledge disposed beneath the pipette housing and having openings through which the pipette rods are disposed, the movable head linearly movable relative to the pipette housing; and
a carriage operable to push the ledge contactable pistons from an upper position out of contact with the lower ledge to a lower position in contact with the lower ledge, wherein in the lower position the carriage is operable to urge the pistons against the lower ledge thereby urging the movable head downwardly.

12. The multi-function dispense head of claim 11 wherein the carriage is attached to the pipette rods and is operable to move the pipette rods linearly through the pipette housing as the carriage moves linearly.

13. The multi-function dispense head of claim 11 further comprising a single motor driving the carriage.

14. The multi-function dispense head of claim 11 wherein the lower ledge has a stepped cross section.

15. The multi-function dispense head of claim 11 wherein the movable head further comprises aspirate tips and wash tips extending from within the movable head, the aspirate tips and wash tips movable with the movable head by the carriage as the carriage pushes the ledge contactable pistons from the upper position to the lower position.

16. The multi-function dispense head of claim 15 further comprising a fluid manifold and a vacuum manifold, the wash tips connectable to a fluid source via the fluid manifold and the aspirate tips connectable to a vacuum source via the vacuum manifold.

17. The multi-function dispense head of claim 1 further comprising a spring return mechanism urging the ejector head to the first position from the second position.

18. The multi-function dispense head of claim 11 wherein the movable head comprises a pair of slots and the pipette housing comprises a pair of screws received in the slots.

19. A multi-function dispense head, comprising:
a pipette housing having pipette rods extending from the pipette housing, the pipette rods removably connectable to pipette tips, and ledge contactable pistons vertically movable within piston openings in the pipette housing;
a movable head having a lower ledge along a bottom portion of the movable head disposed beneath the pipette housing and having openings through which the pipette rods are disposed, the movable head linearly movable relative to the pipette housing; and
a carriage movable along a linear pathway, the carriage attached to pipette rods and operable at a higher extent of the linear pathway to linearly move pipette rods within the pipette housing and operable at a lower extent of a linear pathway to push the ledge contactable pistons from an upper position out of contact with the lower ledge to a lower position in contact with the lower ledge, wherein in the lower position the carriage urges the pistons against the lower ledge thereby lowering the movable head.

20. The multi-function dispense head of claim 19, wherein the movable head further comprises a vacuum manifold connected to aspirate tips extending from the movable head and a fluid manifold connected to wash tips extending from the movable head, the wash and aspirate tips connectable to a fluid source and a vacuum source, respectively, via the manifolds.

\* \* \* \* \*